(12) United States Patent
Lasch et al.

(10) Patent No.: US 11,260,162 B2
(45) Date of Patent: Mar. 1, 2022

(54) AIRWAY SUCTION DEVICE

(71) Applicant: Board of Regents of the University of Texas System, Austin, TX (US)

(72) Inventors: Michael Lasch, Schertz, TX (US); Yusheng Feng, San Antonio, TX (US); Bruce Adams, San Antonio, TX (US); Robert Delorenzo, San Antonio, TX (US); David Cormier, San Antonio, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 278 days.

(21) Appl. No.: 16/098,541

(22) PCT Filed: May 4, 2017

(86) PCT No.: PCT/US2017/031164
§ 371 (c)(1),
(2) Date: Nov. 2, 2018

(87) PCT Pub. No.: WO2017/192919
PCT Pub. Date: Nov. 9, 2017

(65) Prior Publication Data
US 2020/0222598 A1    Jul. 16, 2020

Related U.S. Application Data

(60) Provisional application No. 62/331,954, filed on May 4, 2016.

(51) Int. Cl.
*A61M 1/00*    (2006.01)

(52) U.S. Cl.
CPC ............... *A61M 1/74* (2021.05); *A61M 1/80* (2021.05); *A61M 2205/3331* (2013.01);
(Continued)

(58) Field of Classification Search
CPC .. A61M 2210/0618; A61M 2210/0625; A61M 1/0001; A61M 1/0023; A61M 1/0031; A61M 1/0066; A61M 2205/3331; A61M 2205/3334; A61M 2205/7536; A61M 2210/1032; A61M 2205/3365; A61M 2210/1028; A61M 1/0052; F04D 27/004; F04D 17/16
See application file for complete search history.

(56) References Cited

U.S. PATENT DOCUMENTS 4,429,693 A * 2/1984 Blake .................. A61M 1/0011
604/133
4,898,167 A * 2/1990 Pierce ..................... F04B 45/02
128/205.16
(Continued)

OTHER PUBLICATIONS

International Search Report and Written Opinion issued in Application No. PCT/US2017/031164, dated Jul. 19, 2017.
(Continued)

*Primary Examiner* — Nicholas J Weiss
*Assistant Examiner* — Alessandro R Del Priore

(57) ABSTRACT

Disclosed herein are devices and methods of use of that device that assists in the clearing of the airway of a patient and where the device is portable and able to be used with a single hand.

8 Claims, 5 Drawing Sheets

(52) U.S. Cl.
CPC ............... *A61M 2205/3334* (2013.01); *A61M 2205/7536* (2013.01); *A61M 2210/1032* (2013.01)

(56) References Cited

U.S. PATENT DOCUMENTS

| | | | | |
|---|---|---|---|---|
| 4,930,997 | A * | 6/1990 | Bennett | F04C 18/3441 417/410.1 |
| 4,988,342 | A * | 1/1991 | Herweck | A61M 1/0027 604/321 |
| 6,210,133 | B1 * | 4/2001 | Aboul-Hosn | A61M 60/36 417/423.1 |
| 2003/0163101 | A1 * | 8/2003 | Say | A61M 1/0003 604/319 |
| 2003/0222101 | A1 * | 12/2003 | Chang | A61M 1/80 222/108 |
| 2004/0208756 | A1 * | 10/2004 | Adahan | F04B 53/22 417/360 |
| 2005/0002810 | A1 * | 1/2005 | Gould | F04B 45/02 417/472 |
| 2006/0122558 | A1 * | 6/2006 | Sherman | A61M 1/0031 604/67 |
| 2008/0199357 | A1 * | 8/2008 | Gellman | A61M 1/1015 422/48 |
| 2011/0278296 | A1 | 11/2011 | Martini et al. | |
| 2013/0338559 | A1 * | 12/2013 | Franano | A61M 1/3655 604/4.01 |
| 2016/0106919 | A1 | 4/2016 | Hayter et al. | |
| 2016/0206805 | A1 * | 7/2016 | Hassidov | A61M 3/0212 |
| 2020/0398009 | A1 * | 12/2020 | Chaturvedi | A61M 16/0486 |

OTHER PUBLICATIONS

International Preliminary Report on Patentability issued in Application No. PCT/US2017/031164, dated Nov. 6, 2018.

* cited by examiner

AIRWAY SUCTION DEVICE

CROSS REFERENCE TO RELATED APPLICATIONS

This application is a national phase application under 35 U.S.C. § 371 of International Application No. PCT/US2017/031164, filed May 4, 2017 which claims priority to U.S. Provisional Application Ser. No. 62/331,954 filed May 4, 2016, each of which is incorporated here by reference in its entirety.

FIELD OF THE INVENTION

The present invention relates generally to devices and methods for a device that assists in the clearing of the airway of a patient. More specifically, the present invention relates to devices and methods of use of that device that assists in the clearing of the airway of a patient and where the device is portable and able to be used with a single hand.

BACKGROUND OF THE INVENTION

Without limiting the scope of the disclosed devices and methods, the background is described in connection with devices and methods for clearing the airway of patients.

Military and civilian EMS providers need a lightweight, reliable, and effective means of clearing debris such as saliva and vomitus from the airway of critical patients. Portability, effectiveness, and ruggedness are key attributes for an airway suction device. These are important as combat medics carry everything on their backs.

Currently, there does not exist such a device. Current designs are at least twenty years old and fall short on many aspects since they are developed using poor technology. That is the designs are heavy, bulky, low suction, and contain a short battery life. This results patients suffering serious harm such as aspiration of debris, inability to gain control of airway control, and suffocation death.

In view of the foregoing, it is apparent that there exists a need in the art for a device and method to clear airways of patients, which overcomes, mitigates, or solves the above problems in the art. It is the purpose of this invention to fulfill this and other needs in the art, which will become apparent to the skilled artisan once given the following disclosure.

BRIEF SUMMARY OF THE INVENTION

The present invention, therefore, provides for devices and methods that assist in the clearing of the airway of a patient.

This invention relates to the field of emergency medicine and more particularly to a device, which will aid in the clearing of a critically wounded and bleeding patient. This invention is useful for allowing a doctor, emergency responder, or combat medic to clear patient airway portability and with a single hand. Furthermore, this device is designed to prevent clogs of the airway-clearing device by actively separating solid particulates and liquids in order to continually provide an adequate level of suction. This device has been designed to have an integrated footprint reducing slide able storage container feature that allows the user to collapse the device for transportation and storage, and expand the device for enhanced storage capability and stability when in use. Finally, the device will be comprised of modular sections in order to allow for care in all settings whether it be in the field, during medevac, or care in a hospital. This device also integrated an optimized centrifugal pump design to maximize suction capability, while reducing weight and sound.

For example, during battlefield triage, a combat medic must utilize both hands in order to clear a patient's airway. This is due to the fact that the current standard of care is not ergonomically balanced to allow one-handed operation. By freeing the medic's secondary hand, it becomes possible to treat the patient more efficiently. The rationale behind this device is that the current level of care consists of a mechanical suction device, or electrical suction devices that do not provide adequate levels of suction, ergonomic balance, the ability to separate solid and fluid, or have modular capability.

In summary, the present invention discloses devices and methods directed a device that assists in the clearing of the airway of a patient. More specifically, the present invention relates to devices and methods of use of that device that assists in the clearing of the airway of a patient and where the device is portable and able to be used with a single hand.

BRIEF DESCRIPTION OF THE SEVERAL VIEWS OF THE DRAWINGS

The accompanying drawings, which are incorporated in and form a part of the specification, illustrate a preferred embodiment of the present invention, and together with the description, serve to explain the principles of the invention. It is to be expressly understood that the drawings are for the purpose of illustration and description only and are not intended as a definition of the limits of the invention. In the drawings.

DETAILED DESCRIPTION OF THE INVENTION

Disclosed herein are devices and methods of use of that device that assists in the clearing of the airway of a patient and where the device is portable and able to be used with a single hand. The numerous innovative teachings of the present invention will be described with particular reference to several embodiments (by way of example, and not of limitation).

Figure 1:
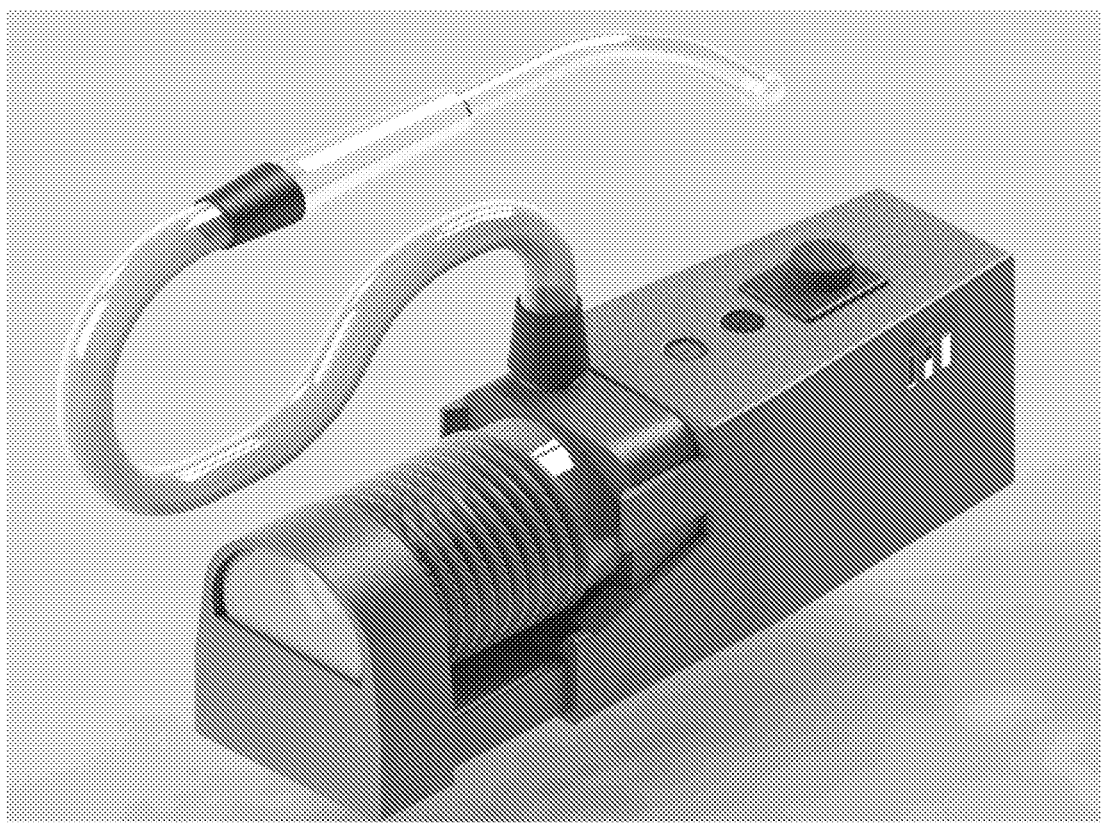
FIG. 1 is a front perspective view of the airway suction device in accordance with the teachings of the present disclosure.

Reference is first made to FIG. 1, a front perspective view of the airway suction device in accordance with the teachings of the present disclosure. Illustrated here is the device showing all the major external components in an embodiment:

1. Collapsible spring-loaded storage container that expands as fluid is inserted. This storage container is attached onto the suction device in a collapsed position. It has a removable seal, which once broken, will allow the container to expand to full size. This expansion will also extend a slide base on the suction device to accommodate for the larger profile. The storage container will be integrated to expand with the collapsible storage bag 2. A pressure sensor combined with an active control system detects changes in pressure in the gas portion of the flow between the hydrophobic filter and the centrifugal pump. As the control system detects a change in pressure, it responds by changing the RPM of the impeller to either increase or decrease the flow rate. It has the ability to reverse the flow in situations where the pressure change can't be resolved through a change in the flow.

3. Optimized centrifugal powered design. The shape and angles of the centrifugal pump are optimized to handle the airflow through this specific device, and provide maximum pressure differential across the pump.

4. Device overdrive functionality. The device has the ability to push the centrifugal pump to a higher RPM state based upon the button press of the user.

5. Hermetically sealed induction based impeller drive system. This drive system allows the removal of hydrophobic filter by making it disposable. The non-disposable portion is hermetically sealed. This sealed portion contains the power supply and drive portions. The disposable portion consists of an iron core, shaft, and impeller. In addition the impeller core is supported through the use of disposable bearings, which have a sliding fit into the induction portion of the driver.

6. A main body which houses any electrical components, the drive system, and controls of the airway suction device. In an embodiment, the storage container is configured to expand with the collapsible storage bag.

7. A suction tube.

Figure 2:
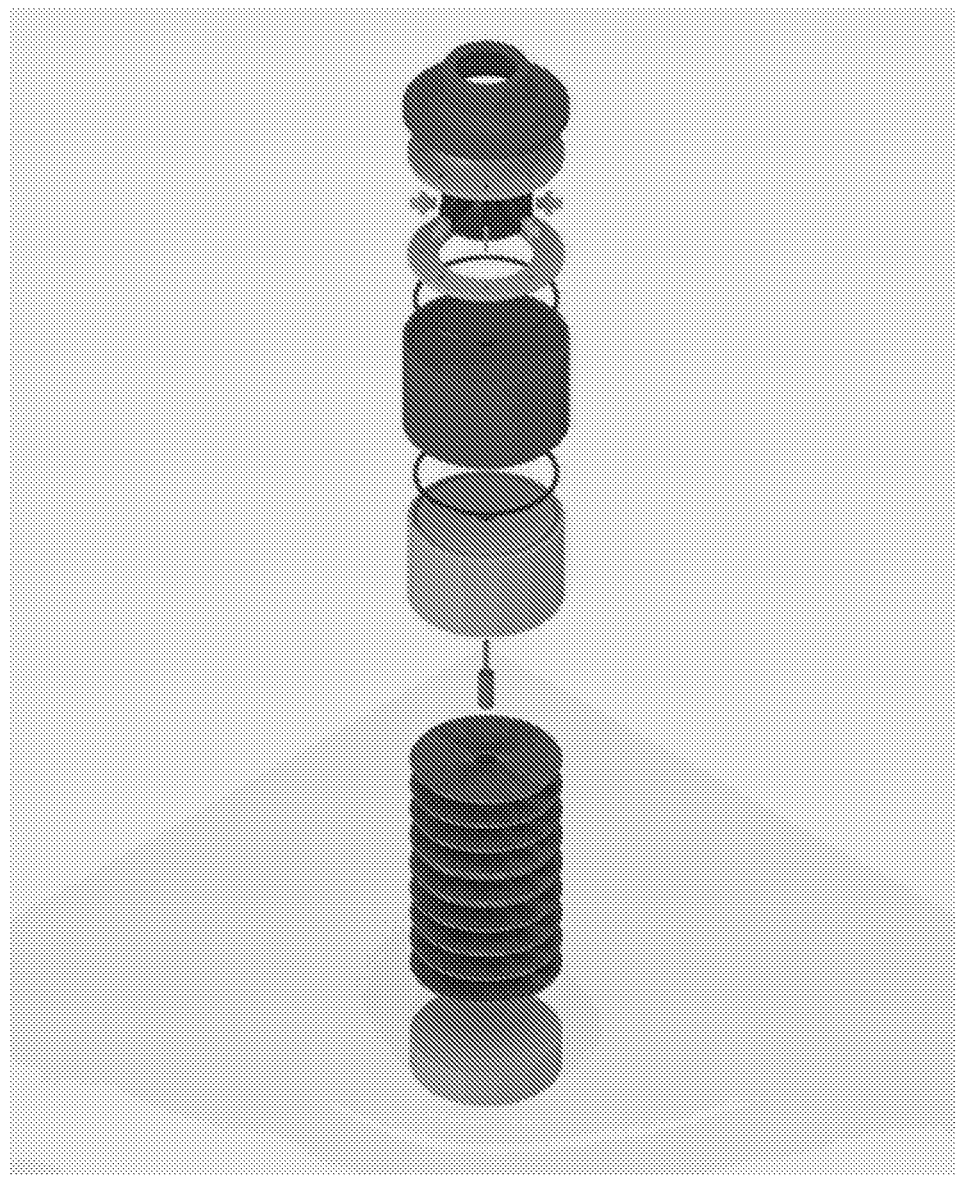
FIG. 2 is an exploded view of the motor of the airway suction device in accordance with the teachings of the present disclosure.

Reference is now made to FIG. 2, an exploded view of the motor of the airway suction device in accordance with the teachings of the present disclosure. This component in an embodiment is designed to allow for a removable impeller shaft and housing in order to allow disposal of these items if they were to become contaminated. The motor driver is hermetically sealed in order to prevent contamination. The impeller in embodiments, relies on a magnetic field from the lower motor coils to suspend it. In addition, in embodiments, there is a magnetic ring under the rubber seals, which the top impeller housing will snap to the lower motor housing. This will allow it to be retained while still being removable.

Figure 3:
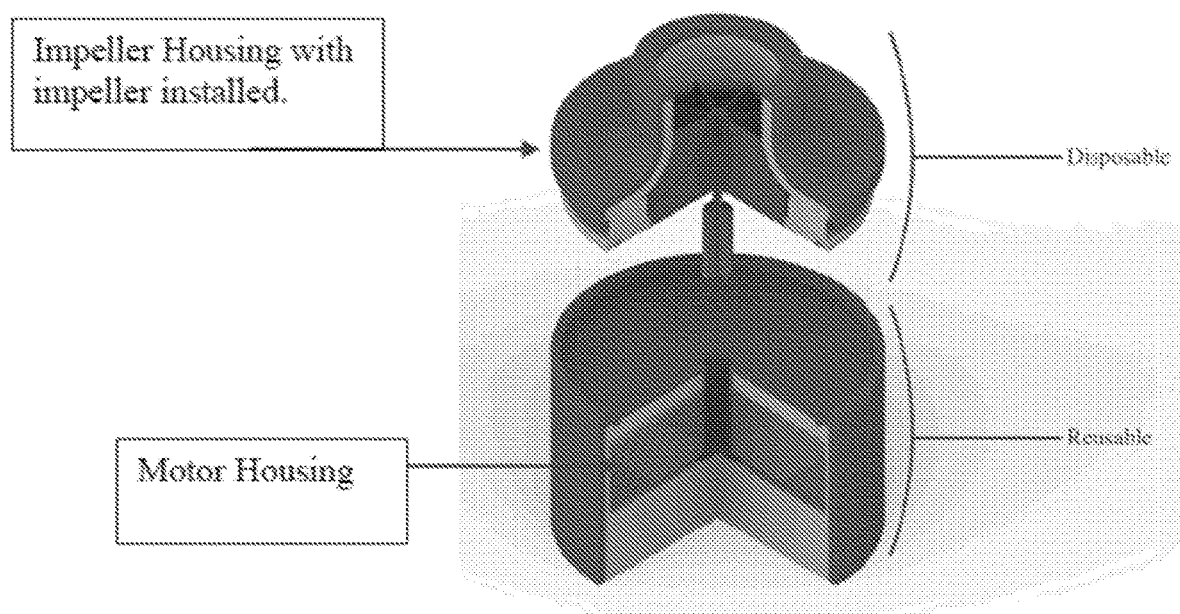
FIG. 3 is a quarter cut view of the motor of the airway suction device in accordance with the teachings of the present disclosure.

Reference is next made to FIG. 3, a quarter cut view of the motor of the airway suction device in accordance with the teachings of the present disclosure. Illustrated in this figure are the disposable components as well as the reusable components. The motor is designed for medical applications. That is, the installation into medical devices. The motor is constructed, in embodiments, so that expensive portions of the motor are protected so that they do not have to be discarded, while letting the lower cost components be discarded to ensure a patient is using a clean and sterile device. The motor drives the suction of the airway suction device.

Figure 4:
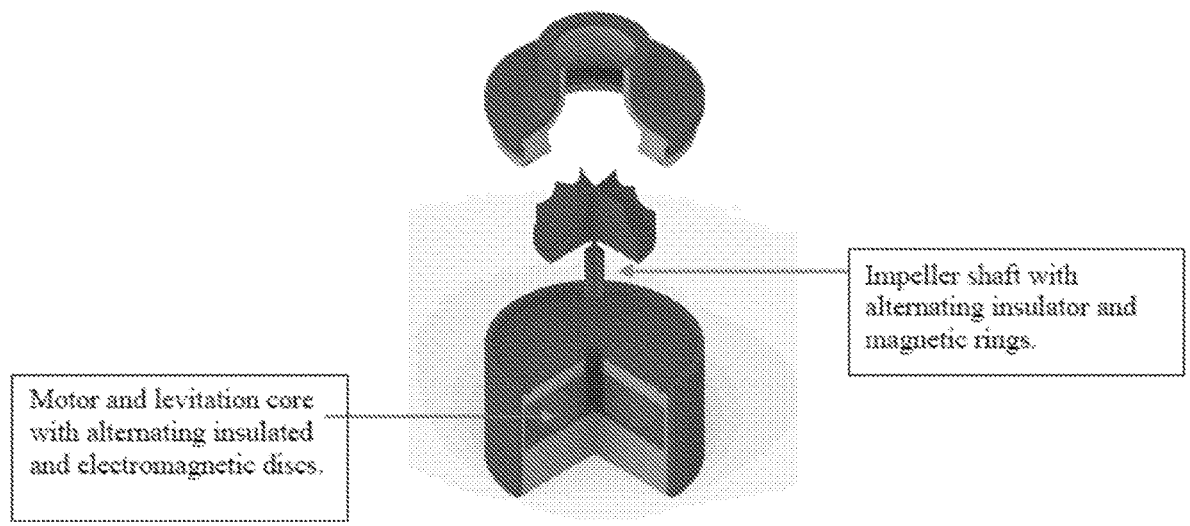
FIG. 4 is a two-part view of the motor of the airway suction device in accordance with the teachings of the present disclosure.

Reference is now made to FIG. 4, a two-part view of the motor of the airway suction device in accordance with the teachings of the present disclosure. Illustrated in this figure is the top impeller housing being a separate piece from the impeller. The impeller blade will be inserted into the motor housing first, and then the housing will be placed on top to create the region which will induce airflow during rotation.

Figure 5:
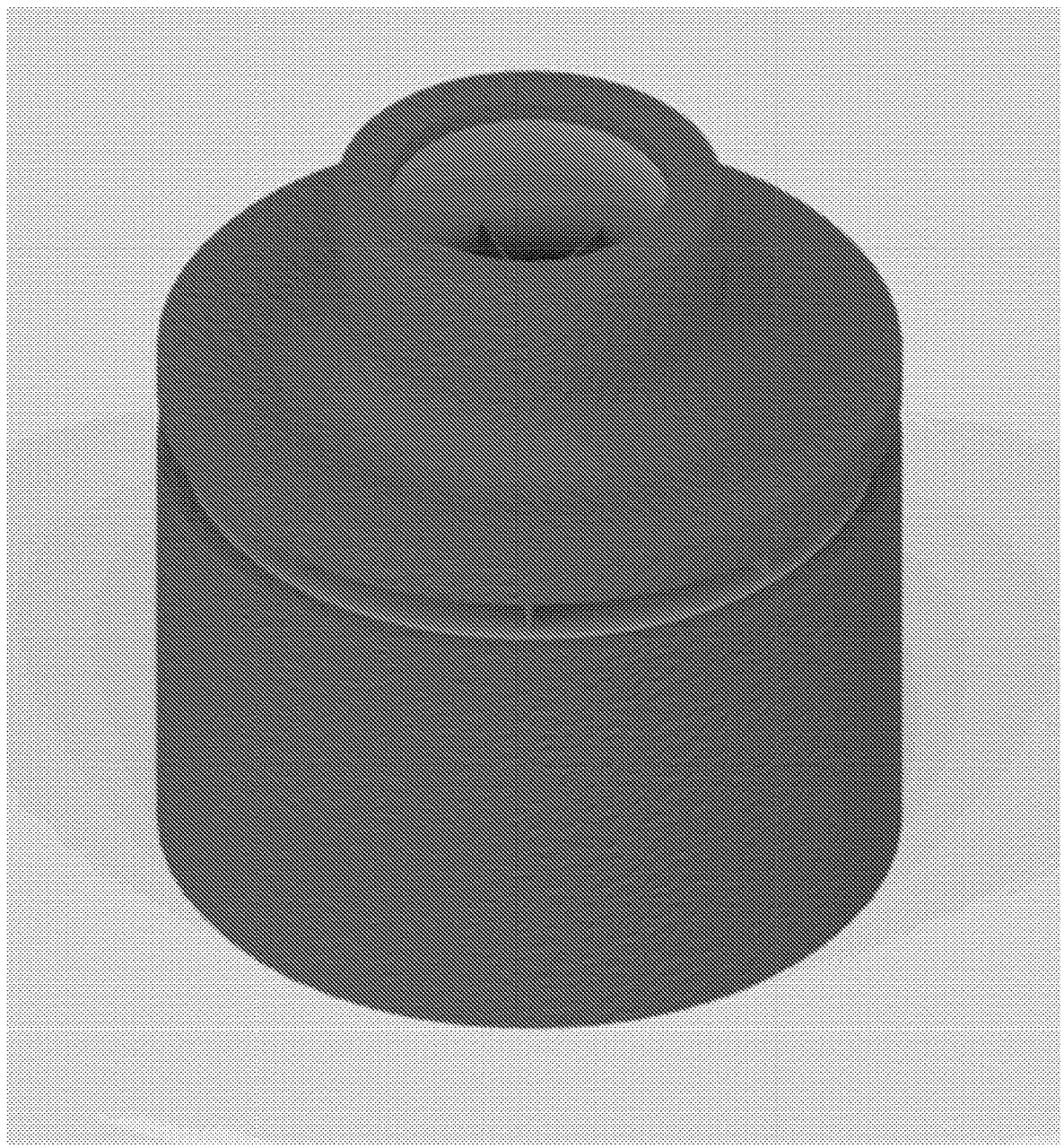
FIG. 5 is a collapsed view of the motor of the airway suction device in accordance with the teachings of the present disclosure.

Reference is lastly made to FIG. 5, a collapsed view of the motor of the airway suction device in accordance with the teachings of the present disclosure. Illustrated in this view is the motor fully assembled. In this configuration, the impeller and impeller housing has already been inserted and locked into place.

The disclosed devices and methods are generally described, with examples incorporated as particular embodiments of the invention and to demonstrate the practice and advantages thereof. It is understood that the examples are given by way of illustration and are not intended to limit the specification or the claims in any manner.

To facilitate the understanding of this invention, a number of terms may be defined below. Terms defined herein have meanings as commonly understood by a person of ordinary skill in the areas relevant to the present invention. Terms such as "a", "an", and "the" are not intended to refer to only a singular entity, but include the general class of which a specific example may be used for illustration. The terminology herein is used to describe specific embodiments of the invention, but their usage does not delimit the disclosed device or method, except as may be outlined in the claims.

Any embodiments comprising a one piece or multi piece device having the structures as herein disclosed with similar function shall fall into the coverage of claims of the present invention and shall lack the novelty and inventive step criteria.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific devices and methods described herein. Such equivalents are considered to be within the scope of this invention and are covered by the claims.

All publications, references, patents, and patent applications mentioned in the specification are indicative of the level of those skilled in the art to which this invention pertains. All publications, references, patents, and patent application are herein incorporated by reference to the same extent as if each individual publication, reference, patent, or patent application was specifically and individually indicated to be incorporated by reference.

In the claims, all transitional phrases such as "comprising," "including," "carrying," "having," "containing," "involving," and the like are to be understood to be open-ended, i.e., to mean including but not limited to. Only the transitional phrases "consisting of" and "consisting essentially of," respectively, shall be closed or semi-closed transitional phrases.

The devices and/or methods disclosed and claimed herein can be made and executed without undue experimentation in light of the present disclosure. While the devices and methods of this invention have been described in terms of preferred embodiments, it will be apparent to those skilled in the art that variations may be applied to the devices and/or methods and in the steps or in the sequence of steps of the methods described herein without departing from the concept, spirit, and scope of the invention.

More specifically, it will be apparent that certain components, which are both shape and material related, may be substituted for the components described herein while the same or similar results would be achieved. All such similar substitutes and modifications apparent to those skilled in the art are deemed to be within the spirit, scope, and concept of the invention as defined by the appended claims.

What is claimed is:

1. An airway suction device comprising:
   (i) a main body comprising a hermetically sealed non-disposable induction drive portion;
   (ii) a disposable portion coupled to the main body comprising an impeller operatively coupled to the induction drive portion and a fluid path comprising a filter and a suction tube fluidically connected to an extendable storage bag via the disposable portion;
   wherein the extendable storage bag is collapsed along its long axis-prior to use and the impeller is configured to move fluid along the fluid path such that the storage bag expands along the long axis during use when being filled with fluid.

2. The device of claim 1, further comprising a pressure sensor combined with an active control system configured to detect changes in pressure in gas flow between the filter and a centrifugal pump.

3. The device of claim 2, wherein said active control system is further configured so as the control system detects a change in pressure, and the control system responds by changing the RPM of the impeller to either increase or decrease the flow rate.

4. The device of claim 2, wherein said active control system is further configured to reverse flow in situations where the pressure change cannot be resolved through a change in the flow.

5. The device of claim 1, wherein said main body is further configured with a collapsible storage container having a slide base which holds the collapsible storage bag and can be extended along a long axis of the device from said main body during use.

6. The device of claim 1, wherein said disposable portion further comprises an iron core and shaft.

7. The device of claim 1, wherein said non-disposable portion further comprises a power supply.

8. An airway suction device comprising:
   (i) a main body comprising a hermetically sealed non-disposable portion comprising an induction drive, a power supply, and an extendable storage container configured to hold an extendable storage bag, the extendable storage container being in a collapsed position prior to use; and
   (ii) a disposable portion coupled to the main body comprising (a) an iron core, (b) shaft, and (c) an impeller operatively coupled to the induction drive portion and a fluid path comprising a suction tube, a filter, and an extendable storage bag, the suction tube being fluidically connected to the extendable storage bag via the disposable portion, wherein the extendable storage bag is collapsed along its long axis prior to use and the impeller is configured to move fluid along the fluid path such that the storage bag expands along the long axis during use when being filled with fluid;
   (iii) a pressure sensor combined with an active control system configured to detect changes in pressure in gas flow between the filter and a centrifugal pump, wherein the active control system is configured to detect a change in pressure and respond by changing the RPM of impeller to either increase or decrease the flow rate.

* * * * *